United States Patent [19]

Smith et al.

[11] Patent Number: 4,808,412

[45] Date of Patent: Feb. 28, 1989

[54] RUMEN-STABLE COMPOSITIONS

[75] Inventors: E. Phillip Smith, Blountville; Stephen H. Wu, Kingsport, both of Tenn.

[73] Assignee: Eastman Kodak Company, Rochester, N.Y.

[21] Appl. No.: 61,755

[22] Filed: Jun. 11, 1987

[51] Int. Cl.⁴ ............................................. A61K 9/00
[52] U.S. Cl. ...................................... 424/442; 424/439
[58] Field of Search ........................ 424/438, 442, 439

[56] References Cited

U.S. PATENT DOCUMENTS

| | | | |
|---|---|---|---|
| 3,041,243 | 6/1962 | Sugimoto et al. | 167/82 |
| 3,380,998 | 4/1968 | Osaka et al. | 260/226 |
| 3,562,806 | 2/1971 | Grant et al. | 424/35 |
| 3,655,864 | 4/1972 | Grass et al. | 424/38 |
| 3,697,640 | 10/1972 | Grant et al. | 424/35 |
| 3,829,564 | 8/1974 | Merry et al. | 424/78 |
| 3,880,990 | 4/1975 | Bauer | 424/19 |
| 3,959,493 | 5/1976 | Baalsrud | 426/2 |
| 4,001,389 | 1/1977 | Fildes | 424/78 X |
| 4,177,255 | 12/1979 | Dannelly | 424/21 |
| 4,181,708 | 1/1980 | Dannelly | 424/19 |
| 4,181,709 | 1/1980 | Dannelly | 424/21 |
| 4,181,710 | 1/1980 | Dannelly et al. | 424/33 |
| 4,196,187 | 4/1980 | Dannelly et al. | 424/21 |
| 4,199,561 | 4/1980 | Roth et al. | 424/32 |
| 4,234,565 | 11/1980 | Flodin et al. | 424/33 |
| 4,268,497 | 5/1981 | Griffin et al. | 424/27 |
| 4,473,545 | 9/1984 | Drake et al. | 424/22 |
| 4,533,557 | 8/1985 | Maruyama et al. | 426/61 |
| 4,595,584 | 6/1986 | Wu et al. | 424/438 |

OTHER PUBLICATIONS

Stephen H. Wu et al.—Controlled Release of Pesticides and Pharmaceuticals, D. H. Lewis, ed., Plenum Press, New York, N.Y., 1981, pp. 319-331.

*Primary Examiner*—Michael Lusignan
*Attorney, Agent, or Firm*—Thomas R. Savitsky; William P. Heath, Jr.

[57] ABSTRACT

A post-rumen effective composition for oral administration to ruminants containing a bioactive substance molecularly dispersed with a basic polymer. The bioactive substance is miscible with the polymer and may be a vitamin, antibiotic, peptide or anti-inflammatory agent. The basic polymer contains from about 1 percent to about 25 percent by weight of nitrogen and is resistant to a pH of greater than about 5 and soluble or swellable at a pH of less than about 3.5.

18 Claims, No Drawings

RUMEN-STABLE COMPOSITIONS

TECHNICAL FIELD

This invention relates to rumen-stable compositions for oral administration of bioactive materials such as medicaments and nutrients to ruminant animals.

BACKGROUND OF THE INVENTION

It is well known in the art that it is desired to have compositions adapted to be orally administered to ruminants and which are beneficial to ruminants after passing the rumen and reaching a post-rumen site, e.g., the abomasum and/or intestines.

In ruminants, ingested feed first passes into the rumen, where it is pre-digested or degraded by fermentation. During this period of fermentation the ingested feed may be regurgitated to the mouth via the reticulum where it is salivated and ruminated. After a period of fermentation regulated by natural processes and variable depending on the animal and the feedstuff, adsorption of digested nutrients starts and continues in the subsequent sections of the digestive tract by the ruminant animal. This process is described in detail by D. C. Church, "Digestive Physiology and Nutrition of Ruminants", Vol. 1, O.S.U. Book Stores, Inc., of Corvallis, Oreg.

The rumen, the largest of the four stomach compartments of ruminants, serves as an important location of metabolic breakdown of ingested foodstuffs through the action of microorganisms which are present therein. Ingested food is typically retained in the rumen for from about 6 to 30 hours or longer in some instances, during which time it is subject to metabolic breakdown by the rumen microorganisms. Much ingested protein material is broken down in the rumen to soluble peptides and amino acids and utilized by the rumen microorganisms. When the rumen contents pass into the abomasum and intestine, the microbial mass is digested, thus providing protein to the ruminant. Thus, the natural nutritional balance of the ruminant animal is primarily a function of the microbial composition and population.

In preparing nutrients and medicaments intended for administration to ruminants, it is important to protect the active ingredients against the environmental conditions of the rumen, i.e., microbial degradation and the effects of a pH of about 5.5-7.0, so the active substance will be saved until it reaches the particular location where adsorption takes place. It is well known that the rate of meat, wool and/or milk production can be increased if sources of growth limiting essential amino acids, and/or medicaments, are protected from alteration by microorganisms residing in the rumen and become available for direct absorption by the animal later in the gastrointestinal tract.

Materials which protect the bioactive agents, i.e., nutrients and medicaments, against degradation by the rumen contents should be resistant to attack by the rumen fluid which contains enzymes or microorganisms but must make the active ingredient available post-rumenally, e.g., in the abomasum or in the small intestine.

Because proteins are subject to breakdown in the rumen, it has been suggested that protein-containing nutrients fed to ruminants be treated so as to permit passage without microbial breakdown through the rumen to the abomasum. Suggested procedures have included coating the protein material, for example, with fats and vegetable oils or with an acid sensitive coating; heat treating of the protein material; reacting the protein material with various compounds such as formaldehyde, acetylenic esters, polymerized unsaturated carboxylic acid or anhydrides and phosphonitrilic halides, etc.

It is well known that all proteins found in animal and plant life are chemical compounds containing different combinations of over 20 amino acids, the number and arrangement of such acids being fixed in any particular protein. Twelve of these amino acids can be synthesized in nutritionally adequate normally present in most animals, but the remaining 10 essential amino acids are not synthesized in sufficient quantities and must be ingested by the animal. Since the proportions of the constituent amino acids in a particular protein cannot be varied, the essential amino acid least in supply limits the amount of that protein which can be produced by the animal. Consequently, for any given diet, there will be a particular essential amino acid which limits the production of protein incorporating that essential amino acid unless, of course, two or more such amino acids are equally limiting.

The appreciation of the above principles leads to the formulation of diets for nonruminant animals which provide the optimum proportion of amino acids and have enable significant increases in protein production to be achieved. In the ruminant, dietary proteins and amino acids are, to a variable extent, broken down to ammonia and various organic compounds by microbial fermentation in the first two compartments of the stomach (the rumen and reticulum). The bacteria and protozoa in these organs utilize these metabolites for their own growth and multiplication and the microbial protein so formed passes on to the abomasum, the compartment of the stomach corresponding to the stomach of nonruminants, where it is partially digested. The process is completed in the small intestine and the amino acids are absorbed. Therefore in many instances it is desirable to protect certain essential amino acids from the microorganisms of the rumen and reticulum and thus deliver such amino acids to the abomasum and small intestine.

It is likewise well-known that some medicaments are more effective when they are protected from the environment of the rumen. See, for example, U.S. Pat. Nos. 3,041,243 and 3,697,640. See also "Controlled-Release Feed Additives for Ruminants: Cellulose-Based Coating Composition for Rumen-Stable Nutrients," Wu, et al., in *Controlled Release of Pesticides and Pharmaceuticals*, D. H. Lewis, ed., Plenum Press, New York, N.Y., 1981, p. 319.

The following patents issued to Dannelly et al., teach the art of formulating rumen-stable pellets for a variety of nutrients and medicaments: U.S. Pat. Nos. 4,177,255; 4,181,708; 4,181,709; 4,181,710; and 4,196,187. These patents disclose the art of formulating rumen-stable pellets employing coating techniques. Specifically these patents teach employing a coating process such as air suspension coating to apply a coating formulation onto a solid substrate containing bioactive materials. To practice the technology disclosed in these patents, cores containing medicaments must be prepared first, for example, by a granulation method and then coated with the rumen-stable coating compositions described in the patents. The disclosed technology is particularly useful for preparing a dosage form with high payload of bioactive materials such as amino acids. However, multiple unit operations must be employed to yield the finished products.

U.S. Pat. No. 3,959,493, issued to Baalsrud et al., teaches rumen-stable products comprising biologically active substances protected with aliphatic fatty acids. U.S. Pat. No. 3,655,864, issued to Grass et al., teaches veterinary compositions permitting post-ruminal delivery of biologically active feed additives, in which the compositions are embedded in or coated by an intimate mixture of glyceryl tristearate with a liquid unsaturated higher fatty acid.

U.S. Pat. No. 4,473,545, issued to Drake et al., teaches an animal feed additive comprising a composite of a relatively insoluble binder, a particulate soluble material and an active material. The particulate material is such that it is readily soluble under a particular range of pH conditions, e.g., dissolution rates at pH 2 and pH 6 in the ratio 12:1. Dissolution of the particulate materials rendered the binder water permeable thus permitting release of the active material.

U.S. Pat. No. 4,533,557 teaches a feed additive for ruminants comprising a mixture in tablet or granule form of at least one biologically active ingredient, chitosan and a protective material such as fatty acids having 14 to 22 carbon atoms.

U.S. Pat. No. 3,880,990, issued to Bauer et al., teaches oral ruminant compositions comprising a medicinal substance encapsulated or embedded in a basic polymer. Such compositions are produced by dispersing the medicinal substance in a first solvent in a finely powdered form and adding thereto a second solvent which is immiscible with the first solvent in which the polymer and medicinal substance are substantially insoluble. In such a conventional polymer/medicament dispersion, activity can be lost due to the presence of dispersed active particles at or near the surface of the compositions which will not survive the environment of the rumen. In addition, at some loadings, water channels can form leading to reduced rumen protection of the active particles.

It would be desirable to have rumen stable compositions that avoid multiple step preparatory methods and retain more activity than compositions of conventionally dispersed bioactive particles in a polymer matrix.

SUMMARY OF THE INVENTION

The present invention is directed to a composition that avoids the aforementioned prior art disadvantages. More specifically, the present invention is directed to a post-rumen effective composition for oral administration to ruminants comprising a bioactive agent molecularly dispersed with a basic polymer, said bioactive agent being miscible with the basic polymer, and said basic polymer being defined as follows:

a physiologically acceptable polymeric substance that is a polymer, copolymer, terpolymer, or mixture thereof that is resistant to a pH of greater than about 5 and soluble or swellable at a pH of less than about 3.5 at the normal temperature of the rumen; said polymeric substance having basic amino groups of aliphatic type or said polymeric substance having basic amino groups of the aromatic type in which the basic amino groups are attached directly to the aromatic ring or is part of the aromatic ring structure; the amount of said basic amino groups in the polymeric substance is that amount capable of generating sufficient ionized groups to render the polymeric substance soluble or swellable at about pH 3.5 or below, but at about pH 5.0 or above, the amount of basic amino groups is insufficient to solubilize the polymeric substance; and the nitrogen content of the polymeric substance is between about 1 percent to about 25 percent by weight.

The composition of the present invention can optionally contain one or more additives which can be biologically inert or act as adjuvants. In many instances the type and amount of additive employed is to control the site and/or rate of release of the bioactive agent.

Other additives include common pharmaceutical excipients and feed ingredients which may be used as release rate modifiers and/or carriers for the composition of the present invention so as to render the composition into a desirable dosage form suitable for feed additive applications.

The present invention is also directed to process for preparing the composition of the invention.

By the term "post-rumen effective" is meant that the composition is rumen stable and that the bioactive agent is released post-rumenally such as in the abomasum or intestine which results in a desired controlled delivery of the bioactive agent; the term "bioactive agent" refers to any biologically active substance such as a nutrient or medicament in which it is desired for such substance to by-pass the rumen in order for delivery to a post-rumen site; the term "molecularly dispersed" refers to the type of dispersion that is present when two or more substances that are miscible with each other are brought into intimate contact; the term "incompatible" is used synomonously with immiscible; the term "compatible" is used synomonously with miscible; the abbreviation "vp" refers to vinylpridine and the abbreviation "st" refers to styrene.

The above-noted definitions apply to both singular and plural as well as all tenses of the defined terms.

DETAILED DESCRIPTION OF THE INVENTION

The composition of this invention can be fabricated, optionally with one or more additives such as excipients or feed additives or ingredients, to solid dosage forms of various shapes and sizes or suspensions in liquid vehicles for oral administration to ruminant animals. Examples are powder, microcapsule, granule, pellet, tablet and bolus as solid dosage forms to be used in feed, and latex-like suspensions to be incorporated in drinking water for ruminant animals or suspension in oil for use in feed manufacturing and mixing. The composition (i.e., the fabricated dosage forms of suitable particle size and/or the suspensions) can be incorporated into feed pellets with a conventional feed pelleting process. The latex-like or suspension-in-oil products may alternatively be coated onto solid animal feeds.

The basic polymeric substances which are useful in this invention are physiologically acceptable and resistant to a pH of greater than about 5 but soluble or swellable at a pH of less than about 3.5 at the normal temperature of the rumen (typically 39° C.). The polymeric substances include polymers, copolymers, and/or terpolymers having basic amino groups of aliphatic type or having basic amino groups of the aromatic type in which the basic amino groups are attached directly to the aromatic ring, or part of the aromatic ring structure. The amount of the basic amino groups in the polymeric substance is capable of generating sufficient ionized groups to render the polymeric substance soluble or swellable at pH 3.5 or below, but at pH 5.0 or above, the amount of basic amino groups is insufficient to solubilize the polymeric substance. The nitrogen content of the polymeric substance is between about 1% to about 25%, preferably between 1.6% to about 16%. The polymeric substances are macromolecules, preferably of sufficient molecular weight to have film-forming properties when the polymer is deposited from a solution after removal of the solvent, or on cooling from a melt. Typical basic polymers useful for this invention are as follows:

A. Polyvinylpyridine derivatives: for example poly(2-vinylpyridine), poly(4-vinylpyridine), poly(2-methyl-5-vinylpyridine), poly(2-ethyl-5-vinylpyridine), and copolymers of these vinyl monomers or blends of these polymers with each other; copolymers of the said vinyl monomers with other vinyl compounds such as esters of acrylic and methacrylic acids, acrylonitrile and styrene monomers, particularly, copoly(2-vinylpyridine/styrene) and copoly(2-methyl-5-vinylpyridine/styrene).

B. Copolymers containing imidazoline modified styrene such as imidazoline modified copoly(styrene-acrylonitrile) (see U.S. Pat. No. 4,199,561), and polystyrenes modified with basic functional groups such as dimethylaminoethyl groups described by Utsumi et al., in Japan J. Pharm. Chem. 32, 802 (1961).

C. Copolymers of acrylic esters wherein at least one of the monomers contains an acid soluble nitrogen-containing group such as morpholino or dimethylamino group in the alcohol portion: for example a terpolymer of methylmethacrylate, 2-(4-morpholino)ethylacrylate, and stearylmethacrylate. (See U.S. Pat. No. 4,234,565.)

D. Copolymers and terpolymers consisting essentially of a basic substituted acrylate or methacrylate, and at least one ethylenically unsaturated compound selected from vinyl aromatic hydrocarbons, vinyl esters, normal and branched chain alkyl esters of acrylic and methacrylic acids and acrylonitrile such as copoly(tert-butylaminoethyl methacrylate/methyl methacrylate 75/25). (See U.S. Pat. No. 3,829,564).

E. Cellulose derivatives containing acyl groups and basic nitrogen-containing functional groups such as N,N-disubstituted aminohydroxypropyl groups, and morpholinobutyryl groups; for example cellulose propionate morpholinobutyrate (CPMB) (see U.S. Pat. No. 3,562,806), cellulose acetate diethylaminohydroxypropyl ether (see German Patent No. 1,493,245).

F. Aminocellulose derivatives such as diethylaminomethylcellulose, 1-piperidyl-ethyl-hydroxyethylcellulose, and benzylamino-ethylhydroxy-ethylcellulose described by Utsumi et al., in J. Pharm. Soc. Japan 78, 115–118, (1958).

G. Aminoacid esters of cellulose or cellulose derivatives; for example cellulose acetate diethylaminoacetate described by Ida et al., in J. Pharm. Soc. Japan 78, 619–623 (1958).

H. Polyvinylamines and copolymers of vinylamines and vinylacetate described by Ida et al. in J. Pharm. Soc. Japan 78, 651–654 (1958).

I. Polyvinylaminoacetals such as polyvinyl-N,N-diethylaminoacetacetal described again by Ida et al. in J. Pharm. Soc. Japan 78, 655–58 (1958).

J. Polyacrylic acid derivatives with basic groups, a polyacrylic acid derivative in which the carboxyl groups are esterified with dimethylaminoethanol or similar amino alcohols.

K. Imidamine polymers or copolymers of methacrylic acid and basic methacrylic acid amides described in Belgian Pat. No. 703,820.

L. Amino derivatives of sugars, saccharides, polyalcohols, starch products described by Ida et al. in J. Pharm. Soc. Japan 78, 501–504 and 616–618 (1958).

All of the above-described polymers can be prepared by processes known in the art. The preparatory methods in the above-identified patents and literature articles are incorporated herein by reference. The numbers following certain copolymers described herein refer to the weight percentage contributed by each of the respective monomers preceding the numbers.

The bioactive agents useful in the compositions of this invention are nutrients and veterinary medicaments having the properties of limited water solubility, forming with the basic polymer(s) a single phase in mutual solvent(s), and intimate miscibility with the basic polymer(s) to yield a uniform, substantially transparent or translucent film after removal of the solvent(s). Typical bioactive materials which can, for example, be used in this invention are as follows:

| | |
|---|---|
| Vitamins: | alpha-tocopherol and its esters such as acid succinate, beta-carotene |
| Antibiotics: | efrotomycin, virginiamycin, lincomycin, bacitracin |
| Peptides: | N—acetyl aspartame |
| Anti-inflammatory: | ibuprofen |

The additives optionally present in the compositions of this invention for the modification of release rate of the bioactives from the basic polymeric substance in an acidic media comprise small molecules or polymers intimately miscible with the basic polymer substances and having the properties of water solubility, pH-sensitivity, or hydrophobicity so as to enhance or retard the release rate of the bioactives from the complex (i.e., composition) in an acidic media. Other additives function as processing aids (e.g., plasticizers and lubricants) and may or may not contribute to release rate modification. Typical examples are given as follows:

| | |
|---|---|
| neutral water-soluble additives: | compatible plasticizers such as triacetin |
| water-soluble acidic additives: | short chain volatile fatty acids, ascorbic acid, aspirin, multi-functional organic acids such as succinic acids, aromatic organic acids such as phthalic acid, phenol |
| hydrophobic additives: | water-insoluble long-chain fatty acids containing for example 8 to 32 carbon atoms; food emulsifiers such as monoglycerides |
| surfactants: | cholic acid and its derivatives; phosphated monoglycerides. |

Other additives include pharmacologically acceptable excipients and carriers that are miscible or immiscible with said polymer substance such as lactose, talc or TiO2. It should be noted that a given additive may perform more than one function, for example, lactose can act as an excipient and as a release rate modifier.

The composition of the present invention contains an amount of bioactive agent to be effective for it's intended purpose. Typically, the composition of the present invention contains between about 0.01 percent and about 50 percent by weight of bioactive agent; preferably between about 10 percent and about 40 percent of bioactive agent. The composition of the present invention typically contains between about 50 percent and about 99.99 percent by weight of the basic polymer; preferably between about 60 percent and about 90 percent of basic polymer. The above-described percentages are based on the weight of the two components (i.e., bioactive agent plus basic polymer).

For a composition containing one or more additives, typically such composition contains between 0 and about 95 percent by weight of one or more additives; preferably between about 20 and about 90 percent by weight of additive(s) (percentages are based on the weight of bioactive agent plus basic polymer plus additive(s)). For plasticizer additives, e.g., triacetin, a preferred amount of such additive(s) is between about 5 and about 35 percent by weight of the basic polymer. For incompatible filler additives, e.g., lactose, a preferred amount of such additive(s) is between about 50 and about 95 percent by weight (percentages are based on the weight of the ultimate composition).

In the process of this invention, the basic polymer may be dissolved in a suitable organic solvent or a mixture of solvents which would be physiologically acceptable in the event there are residues upon evaporation of the solvent(s). Suitable solvents include lower alkyl alcohols, such as methanol; acetone; methylene chloride; and the like. The bioactive agent and, optionally, one or more release-rate modifier additives are then blended into the polymer solution to form a single phase solution. The solution is then ready for solvent removal to yield a rumen-stable composition. The composition may be milled or cut to form fine granules for mixing with feed. The solution also may be blended with one or more other additives such as common pharmaceutical excipients or feed ingredients to form dosage forms such as granules or pellets by conventional granulation and feed pelleting processes. The solution may also be used to form a latex-like suspension by adding water to the organic solution to form an oil-in-water emulsion and then removing the solvents from the emulsion.

In another process of this invention, basic polymer, compatible bioactive agent and additives (such as release-rate modifiers and pharmaceutical excipients) may be blended and extruded at a temperature such that the polymer and the compatible materials form a homogeneous melt phase, and after solidifying, the extrudate may be milled or cut by conventional particle size reduction methods to form granules in the desirable particle size range.

The present invention is illustrated by the following examples; however, these examples should not be interpreted as a limitation on the scope of the invention.

EXAMPLE 1

This example illustrates a rumen-stable composition consisting of copoly(2-vinylpyridine/styrene, 80/20) ("2-vp/st, 80/20") and efrotomycin.

A 10% polymer solution (weight/volume (w/v)) was prepared by dissolving 16 grams of 2-vp/st (80/20) powder in 160 milliliters (ml) of acetone/methanol (85 percent by weight acetone and 15 percent by weight methanol "85/15") while stirring. The polymer solution appeared to be a yellowish transparent solution. A 10% solution of efrotomycin was prepared by dissolving 4 grams of bulk efrotomycin (containing approximately 78% active efrotomycin) in 40 milliliters (ml) of acetone/methanol (85/15). The solution exhibited a dark brown color. The efrotomycin solution was then added to the polymer solution while stirring. No precipitate or phase separation was observed and the solution appeared to be transparent and exhibited light brown color. Efrotomycin may be added directly to the polymer solution to obtain the same result. These results demonstrate that efrotomycin and the polymer are miscible in the solution phase.

A portion of the polymer/efrotomycin solution was poured into an evaporating dish to allow solvent evaporation at room temperature. A uniform, transparent, dry, dark brown film was formed after the solvent was substantially removed.

A small polymer/efrotomycin film (approximately 4×4×0.5 millimeters (mm)) was extracted in 50 ml of pH 5.4 simulated rumen fluid containing sodium acetate and acetic acid. After 24 hours., the film remained intact and the buffer solution remained clear. Essentially no efrotomycin was detected in the supernatant by a high performance liquid chromatography (HPLC) method. Another piece of polymeric film of similar dimensions was extracted in 50 ml of pH 2.9 simulated abomasal fluid containing citric acid and sodium phosphate. Initially, the polymeric matrix started to gel and the solution became light yellowish. After approximately 60 minutes (min), the polymeric matrix was essentially dissolved to form a slightly cloudy yellowish solution due to low solubility of efrotomycin (less than 0.05 milligrams (mg)/ml at pH 2.9 at 25° C.). Small portions of the supernatant were filtered and analyzed for efrotomycin by a HPLC method during the course of extraction. The results are given as follows in Table 1 and compared with the release of bulk drug in granule form containing the same amount of efrotomycin.

TABLE 1

| Extraction Time | Percent Release of Efrotomycin from Bulk Drug | Percent Release of Efrotomycin from Polymer Matrix |
| --- | --- | --- |
| 15 min | 53 | 10.0 |
| 30 min | 48 | 16.0 |
| 45 min | 51 | 35.0 |
| 60 min | 62 | 59.0 |
| 90 min | 62 | 79.0 |
| 120 min | 60 | 81.0 |

EXAMPLE 2

The antimicrobial property of the polymeric matrix (i.e., a composition of the invention) can be demonstrated by a microbiological cylinder plate assay which is briefly described as follows:

1. Inoculate agar with heat shocked Bacillus megaterium (ATCC 10778) spore suspension (ATCC 10778) and distribute the agar evenly on the test plate containing the uninoculated agar base layer in a petri dish (20x100 mm).
2. Place a sterilized cylinder (stainless steel, 8 mm outside diameter (od), 6 mm inside diameter (id), and 10 mm height) on each plate.

3. Fill the cylinder with the standard or assay solutions (pH 2.9 buffer extract) and incubate the plates 20 to 24 hours in a 28° C. incubator.
4. Measure the diameter of the zone of inhibition and compare the zone diameters for the control and the tested solutions.

pH 2.9 buffer solutions and extracts described in Example 1 and a standard efrotomycin solution (10 micrograms (mcg)/ml) were tested for antimicrobial activities using the above-described assay method. To enhance the solubility of efrotomycin in buffer extracts, a small amount of bovine bile was added to the buffer extracts and then the solutions were diluted to approximately 10 mcg/ml.

0.2 ml each of the standard solution and pH 2.9 buffer extracts with and without bile were used in the assay method.

Both pH 2.9 buffer solutions without efrotomycin gave no zone of inhibition. However, pH 2.9 buffer extract with bile gave a zone of inhibition with a diameter similar to the standard solution (approximately 1 centimeter (cm)); pH 2.9 buffer without bile gave a ditinctive but smaller zone diameter. These results show that the polymeric matrix (i.e., composition) described in Example 1 will preserve the antimicrobial property of efrotomycin after post-ruminal delivery.

EXAMPLE 3

This example illustrates the rumen-stability and abomasal release characteristics of compositions comprising copoly(2-vp/st, 80/20)/efrotomycin in the range of 90/10 to 60/40 by weight. The test samples have similar dimensions (about 4×4×0.5 mm) as given in Example 1. The results are shown in Table 2.

TABLE 2

| polymer/efrotomycin ratio | percent rumen protection (pH 5.4, 24 hrs.) | percent abomasal release (pH 2.9, 2 hrs.) |
|---|---|---|
| 90/10 | 100 | 83.0 |
| 80/20 | 100 | 80.0 |
| 70/30 | 100 | 86.0 |
| 65/35 | 100 | 73.0 |
| 60/40 | 100 | 10.0 |
| 50/50 | 100 | 14.0 |
| 40/60 | 100 | 6.0 |

EXAMPLE 4

This example illustrates the use of homopolymer in this invention and the effect of copolymer composition on the release characteristics of the composition.

Polymeric films were prepared as described in Example 1 in which a homopolymer, poly(2-vinylpyridine), or copoly(2-vp/st, 65/35) was used. The films gave greater than 90% rumen protection at pH 5.4 after 24 hrs. extraction.

Results of efrotomycin release from the polymeric films in pH 2.9 buffer are shown as follows in Table 3:

TABLE 3

| Time, min. | Percent Release (homopolymer, poly(2-vp)) | Percent Release (copoly(2-vp/st). 65/35) |
|---|---|---|
| 15 | 10.0 | 1.0 |
| 30 | 26.0 | 1.0 |
| 45 | 35.0 | 1.0 |
| 60 | 59.0 | 4.0 |
| 90 | 79.0 | 5.0 |
| 120 | 80.0 | 8.0 |

EXAMPLE 5

This example illustrates the miscibility of poly(2-vp/st, 80/20) and typical bioactive materials in solution phase and after removal of the solvent (matrix phase). The procedures used were similar to those described in Example 1. The results are in Table 4.

TABLE 4

| Bioactives | Solvent | Polymer/Bioactive(s) Ratio, weight/weight (w/w) | Miscibility Solution Phase | Miscibility Matrix Phase |
|---|---|---|---|---|
| virginiamycin | methanol | 90/10 | c[1] | M[2] |
| | | 80/20 | c | M |
| | | 70/30 | c | M |
| | | 60/40 | c | M |
| | | 50/50 | c | M |
| virginiamycin/ efrotomycin | methanol | 90/5/5[3] | c | M |
| | | 80/10/10 | c | M |
| | | 80/15/15 | c | M |
| lincomycin | methanol | 90/10 | c | M |
| | | 80/20 | c | s.H.[4] |
| bacitracin | methanol | 90/10 | c | M |
| | | 80/20 | c | M |
| | | 70/30 | c | M |
| | | 60/40 | c | M |
| | | 50/50 | c | M |
| ascorbic acid | methanol | 90/10 | c | M |
| | | 80/20 | c | M |
| | | 70/30 | c | M |
| | | 60/40 | c | M |
| | | 50/50 | c | M |
| acetyl aspartame | methanol | 90/10 | c | M |
| monensin sodium salt | methanol | 90/10 | c | IM[5] |
| | | 80/20 | | |

[1]c = compatible, a transparent single phase solution wherein the bioactive agent is molecularly dispersed in the polymer solution.
[2]M = miscible, transparent or translucent film wherein the bioactive agent is molecularly dispersed in the polymer.
[3]ratio of polymer to respective bioactives, i.e., polymer/virginiamycin efrotomycin.
[4]s.H. = slightly hazy, not all bioactive agent is molecularly dispersed.
[5]IM = immiscible, bioactive agent not molecualrly dispersed.

EXAMPLE 6

This example illustrates the use of the additive, lactose, as a noncompatible excipient and a release rate modifier for the formulation of a granule dosage form.

A solution of poly(2-vp/st, 80/20) was prepared by dissolving 30 grams of the polymer in about 100 ml of ethanol/water (20/1, volume/volume (v/v)). ten grams of efrotomycin bulk drug was then added to the polymer solution while stirring to yield a dark brown transparent solution. 400 grams of lactose were then admixed with the polymer/efrotomycin solution in a planetary mixer or in a kneader to make a wet dough until the solution was uniformly distributed. The dough was allowed to dry in a hood or placed in an oven under reduced pressure to remove the solvent. The dry product was then milled to reduce the particle size to the desirable range such as −20/+60 mesh according to the U.S. mesh size standard.

One gram of the granules (−20/+30 U.S. standard mesh size) was extracted in 50 ml of pH 5.4 buffer solution for 24 hr. The supernatant was analyzed for efrotomycin by a HPLC method. No efrotomycin was detected in the extract. Another one gram sample was extracted in pH 2.9 buffer. After 15 min., the granules completely dissolved in the solution. These results indicate that the granules exhibit the desirable rumen-stability and abomasal release characteristics.

EXAMPLE 7

This example illustrates the use of an extrusion process for granulation of the dough prepared as in Example 6. The use of lactose in the formulation to enhance the release rate of efrotomycin is also demonstrated.

The wet dough as prepared in Example 6 was extruded through an extruder equipped with a multiple perforated die (diameter of the openings: 1-2 mm). The extrudates were cut at the die face with a rotating knife at a speed which was adjusted according to the extrusion rate so as to yield pellets with an aspect ratio (length:diameter ratio) such as 1:1 to 1.5:1. The extrudates may be dried first and then fractured by conventional particle size reduction processes to the desired particle size range. Another three doughs were also prepared as described in Example 6 except adding 25 and 35% of triacetin, and 25% ascorbic acid to replace an equal amount of polymer. The doughs were then extruded, dried, and milled to yield granular products. One-gram each of the products (particle size: −20/+30 mesh) was evaluated for rumen-stability and abomasal release using simulated buffer extraction tests. Results are shown in Table 5. All samples exhibited greater than 90% protection for efrotomycin after 24 hours extraction in pH 5.4 buffer at 39° C. The release data indicate that the granules of each preparation completely dissolved in pH 2.9 buffer. However, a similar granular sample as prepared in Example 1 and 10 without lactose exhibited slower release rate.

rumen-stability. No significant amount of lysineHCl, methionine as well as efrotomycin was detected in the extract. The pellets were then extracted in pH 2.9 buffer for 60 min. to test abomasal release. In 20 min., the polymeric coating disintegrated to allow dissolution of the core materials, and efrotomycin was detected in the buffer extract.

These results demonstrate that the polymeric/efrotomycin complex can be formulated into the rumen-stable coating for the preparation of rumen-protected products.

EXAMPLE 9

This example illustrates the use of compatible additives in the compositions to alter the release rate of bioactives from the polymer matrix in an acidic medium.

85 grams of poly(2-vp/st, 80/20) powder were blended with 45 grams of triacetin (liquid) in a planetary mixer to yield a damp mass. The damp mass was then extruded at about 100° C. through a multiple perforated die in an extruder equipped with a steam jacket. The extrudate could be re-extruded if necessary to obtain a uniform, translucent, rubbery, noodle-like product. 20 grams of efrotomycin bulk drug (about 78% active) were then blended with the rubbery product and the mixture was extruded at 100° C. to yield a uniform dark brown rubbery extrudate. The rubbery material was cooled to −78° C. using dry ice and milled to approximately −20/+30 mesh. The granules are transparent and exhibit one single phase.

75 mg of the granules were extracted in 75 ml of pH 5.4 buffer at 39° C. for 24 hours. The supernatant was analyzed for efrotomycin by a HPLC method. No significant amount of efrotomycin was detected. Another sample of granules (25 mg) was extracted in 75 ml of pH 2.9 buffer at 39° C. for about one hour. All granules

TABLE 5

| Extraction Time, min. | Pecent Release | | | | |
|---|---|---|---|---|---|
| | P/F* (80/20) | P/F/L* (30/10/400) | P/F/A/L* (22.5/10/10.5/400) | P/F/T/L* (22.5/10/7.5/400) | P/F/T/L* (19.5/10/10.5/400) |
| 5 | 1.3 | 51 | 38 | 50 | 43 |
| 10 | 5.9 | 90 | 90 | 83 | 80 |
| 15 | 12.2 | 90 | 91 | 91 | 85 |
| 25 | 24.8 | 91 | 90 | 90 | 90 |
| 45 | 63.3 | 90 | 89 | 89 | 89 |
| 60 | 82.4 | 89 | 89 | 89 | 89 |

*P = poly(2-vp/st 80/20); F = efrotomycin;
L = lactose; T = triacetin; A = ascorbic acid
Note:
Numbers under the composition components indicate the weight ratios of the respective components.

EXAMPLE 8

This example illustrates the incorporation of copoly(2-vp/st, 80/20)/efrotomycin in the rumen-stable coating for the preparation of rumen-protected products such as rumen-protected amino acids.

A coating dope was prepared by (1) dissolving 29.6 grams of coply(2-vp/st, 80/20) and 5.9 grams of efrotomycin bulk drug in 500 ml of acetone/methanol (85/15 v/v). (2) adding 4.7 grams of stearic acid to the polymer solution until it was completely dissolved, and then (3) dispersing 59.7 grams of talc (pharmaceutical grade) into the solution while maintaining stirring.

In an air-suspension coater, 170 grams of lysineHCl and methionine containing pellets were coated with the said coating dope to a coating level of 15% by weight. A sample of coated pellets (1.0 gram) was extracted in 50 ml of pH 5.4 buffer for 24 hours to determine the essentially dissolved about 45 min.

These results show that the granules produced by the extrusion process without using solvent exhibit miscibility and also retain the desirable rumen-stability and abomasal release characteristics.

EXAMPLE 10

This example illustrates the use of miscible additives to modify the release rate of efrotomycin.

A polymer solution was prepared by dissolving 3.5 to 4.0 grams of either poly(2vp/st, 80/20) or poly(2-methyl-5-vinylpyridine, 80/20) "poly(2m5vp/st, 80/20)" in approximately 60 ml methylene chloride while stirring. One gram of efrotomycin bulk drug (about 78% active) was added to the polymer solution until it dissolved. 0.5 gram of ascorbic acid, oleic acid or triacetin were then added to the solution. Each solution remained transparent after adding the respective additive. The solutions were poured into molds (9.0 cm in diameter, 1.3 cm in depth) to allow evaporation of the solvent at ambient temperature. The dry films were milled to yield the products in a granular form.

The rumen-stability and abomasal release characteristics of the products were evaluated as described in the previous examples. The results are tabulated in Table 6.

TABLE 6

| Extraction Time, Min. | P(1)/F* (80/20) | P(1)/F/A* (70/20/10) | P(1)/F/O* (70/20/10) | P(1)/F/T* (70/20/10) | P(2)/F* (80/20) |
|---|---|---|---|---|---|
| Release at pH 2.9, % of Total: | | | | | |
| 5 | 1.3 | 0.2 | 1.4 | 3.0 | 1.8 |
| 10 | 5.9 | 10.7 | 2.7 | 7.7 | 12.1 |
| 20 | 21.4 | 31.8 | 20.9 | 18.7 | 26.6 |
| 30 | 33.9 | 58.9 | 19.9 | 30.8 | 44.8 |
| 45 | 63.3 | 89.9 | 36.9 | 53.0 | 60.0 |
| 60 | 82.4 | 95.1 | 60.1 | 71.7 | 85.1 |
| 90 | 94.6 | 98.4 | 89.1 | 90.3 | 89.6 |
| 120 | 94.1 | 97.6 | 89.9 | 92.5 | 88.9 |
| Protection at pH 5.4, % of Total: | | | | | |
| 24 hr | 99.7 | 99.2 | 97.5 | 99.4 | 99.0 |

*P(1) = poly(2vp/st, 80/20); P(2) = poly(2m5vp/st, 80/20);
F = efrotomycin; A = ascorbic acid; O = oleic acid;
T = triacetin
Note:
The numbers under the composition components represent the respective weight ratios.

These results demonstrate that a hydrophilic compatible additive such as ascorbic acid enhances the release rate, a hydrophobic additive such as oleic acid retards the release rate, and a neutral water soluble additive such as triacetin does not affect the release rate significantly.

EXAMPLE 11

This example illustrates the rumen-stability and abomassal release characteristics of the compositions comprising; cellulose propionate morpholinobutyrate (CPMB)/efrotomycin, CPMB/virginiamycin, cellulose isobutyrate morpholinobutyrate (CIBMB)/efrotomycin, CIBMB/virginiamycin. The film samples were prepared using procedures substantially similar as described in Example 1. 10-20 mg/100 ml each of the products (particle size −20/+30 mesh) was evaluated for rumen-stability and abomassal release using simulated buffer extraction tests. The results are shown in Table 7.

TABLE 7

| Polymer/ Bioactive | Polymer/ Bioactive Ratio w/w | Solvent Used for Film Preparation | Percent Rumen Protection pH 5.4 24 hrs. | Percent Abomasal Release pH 2.9 | |
|---|---|---|---|---|---|
| | | | | 30 min | 1 hr |
| CPMB/ Efrotomycin | 80/20 | Acetone/ Methanol (85/15) | 97 | 36 | 82 |
| CPMB/ Virginiamycin | 80/20 | Acetone/ Methanol (85/15) | 81 | 38 | 72 |
| CIBMB/ Efrotomycin | 80/20 | Methylene Chloride | 94 | 109 | 111 |
| CIBMB/ Virginiamycin | 80/20 | Methylene Chloride | 87 | 39 | 63 |

The invention has been described in detail with particular reference to preferred embodiments thereof, but it will be understood that variations and modification can be effected within the spirit and scope of the invention.

We claim:

1. A post-rumen effective composition for oral administration to ruminants comprising between about 0.01 percent and about 50 percent by weight of a bioactive agent molecularly dispersed with between about 50 percent and about 99.99 percent by weight of a basic polymer, said bioactive agent being miscible with the basic polymer, and said basic polymer being defined as follows:

a physiologically acceptable polymeric substance that is a polymer, copolymer, terpolymer, or mixture thereof that is resistant to a pH of greater than about 5 and soluble or swellable at a pH of less than about 3.5 at the normal temperature of the rumen;
said polymeric substance having basic amino groups of aliphatic type or said polymeric substance having basic amino groups of the aromatic type in which the basic amino groups are attached directly to the aromatic ring or is part of the aromatic ring structure;
the amount of said basic amino groups in the polymeric substance is that amount capable of generating sufficient ionized groups to render the polymeric substance soluble or swellable at about pH 3.5 or below, but at about pH 5.0 or above, the amount of basic amino groups is insufficient to solubilize the polymeric substance;
the nitrogen content of the polymeric substance is between about 1 percent to about 25 percent by weight, and wherein said basic polymer is selected from the group consisting of poly(2-vinylpyridine); poly(4-vinylpyridine);
poly(2-methyl-5-vinyl-pyridine);
poly(2-ethyl-5-vinylpyridine);
copoly(2-vinylpyridine/styrene);
copoly(2-methyl-5-vinylpyridine/styrene);
imidazoline modified copoly(styrene-acrylo-nitrile);
a terpolymer of methylmethacrylate, 2-(4-morpholino)ethylacrylate, and stearylmethacrylate;
copoly(tert-butylaminoethyl methyacrylate/methyl methacrylate 75/25);
cellulose propionate morpholinobutyrate;
cellulose acetate diethylaminohydroxypropyl ether;
diethylaminomethylcellulose;
1-piperidyl-ethyl-hydroxyethylcellulose;
benzylamino-ethyl-hydroxy-ethylcellulose;
cellulose acetate diethylaminoacetate; and
polyvinyl-N,N-diethylaminoacetacetal.

2. A process for preparation of the composition of claim 1 comprising dissolving the basic polymer and bioactive agent in a suitable physiologically acceptable solvent or mixture of solvents to form a single phase solution and then removing the solvent.

3. The process of claim 2 wherein a plasticizer is blended with the basic polymer and bioactive agent.

4. A process for preparation of the composition of claim 1 comprising blending the basic polymer and the bioactive agent at a temperature such that the polymer and the bioactive agent form a homogeneous melt phase.

5. The composition of claim 1 wherein said bioactive agent is selected from the group consisting of vitamins, antibiotics, peptides, and anti-inflammatory agents.

6. The composition of claim 1 wherein said bioactive agent is selected from the group consisting of alpha-tocopherol and its esters; beta-carotene; efrotomycin; virginiamycin; lincomycin; bacitracin; N-acetyl aspartane; and ibuprofen.

7. The composition of claim 1 wherein said basic polymer is selected from the group consisting of copoly(2-vinylpyridine/styrene, 80/20); copoly(2-methyl-5-vinylpyridine/styrene, 80/20); and poly(2-vinylpyridine).

8. The composition of claim 1 wherein said basic polymer is cellulose propionate morpholinobutyrate or cellulose isobutyrate morpholinobutyrate.

9. The composition of claim 1 in the form of a powder, microcapsule, granule, pellet, tablet, bolus, coating, a late-like suspension, or a suspension in oil.

10. The composition of claim 1 wherein the amount of bioactive agent is between about 10 and about 40 percent by weight and the amount of basic polymer is between about 60 and about 90 percent by weight.

11. The composition of claim 1 containing between 0 and about 95 percent by weight of one or more additives.

12. The composition of claim 11 wherein said additives are selected from the group consisting of neutral water-soluble additives; water-soluble acidic additives; hydrophobic additives; and surfactants.

13. The composition of claim 11 wherein said additives are selected from the group consisting of compatible plasticizers; short chain volatile fatty acids; ascorbic acid; aspirin; multi-functional organic acids; aromatic organic acids; water-insoluble long-chain fatty acids; food emulsifiers; cholic acid and its derivatives; phosphated monoglycerides; and pharmaceutical excipients.

14. The composition of claim 11 wherein said additive is selected from the group consisting of triacetin, succinic acids, phthalic acid, phenol, oleic acid; monoglycerides; lactose and talc.

15. The composition of claim 11 wherein the amount of one or more additives is between about 20 and about 90 percent by weight.

16. The composition of claim 11 containing a plasticizer additive in an amount between about 5 and about 35 percent by weight of the basic polymer.

17. The composition of claim 11 containing between about 50 and about 95 percent by weight of an incompatible filler additive.

18. The process of claim 4 wherein a plasticizer is blended with the basic polymer and bioactive agent.

* * * * *